(12) United States Patent
Bert et al.

(10) Patent No.: US 8,299,448 B2
(45) Date of Patent: Oct. 30, 2012

(54) DETERMINATION OF CONTROL PARAMETERS FOR IRRADIATION OF A MOVING TARGET VOLUME IN A BODY

(75) Inventors: Christoph Bert, Aschaffenburg (DE); Eike Rietzel, Weiterstadt (DE); Gerhard Kraft, Darmstadt (DE)

(73) Assignees: GSI Helmholtzzentrum fuer Schwerionenforschung GmbH, Darmstadt (DE); Siemens AG, Munich (DE)

(*) Notice: Subject to any disclaimer, the term of this patent is extended or adjusted under 35 U.S.C. 154(b) by 415 days.

(21) Appl. No.: 12/532,590

(22) PCT Filed: Feb. 19, 2008

(86) PCT No.: PCT/EP2008/001279
§ 371 (c)(1),
(2), (4) Date: Nov. 24, 2009

(87) PCT Pub. No.: WO2008/116535
PCT Pub. Date: Oct. 2, 2008

(65) Prior Publication Data
US 2010/0108903 A1 May 6, 2010

(30) Foreign Application Priority Data

Mar. 23, 2007 (DE) .......................... 10 2007 014 715
Feb. 8, 2008 (DE) .......................... 10 2008 008 358

(51) Int. Cl.
*A61N 5/00* (2006.01)
*A61N 5/10* (2006.01)

(52) U.S. Cl. .............. 250/492.3; 250/396 R; 250/492.1; 250/493.1; 250/505.1; 378/65; 378/125; 600/1; 600/3

(58) Field of Classification Search .............. 250/396 R, 250/492.1, 493.1, 505.1; 378/65, 128; 600/1, 600/3
See application file for complete search history.

(56) References Cited

U.S. PATENT DOCUMENTS 5,017,789 A * 5/1991 Young et al. .......... 250/396 ML
(Continued)

FOREIGN PATENT DOCUMENTS

DE 102005063220 A 6/2007
(Continued)

OTHER PUBLICATIONS

Engelsman, Martijn et al.: "Target volume dose considerations in proton beam treatment planning for lung tumors", *Med. Phys.* 32 (12), Dec. 2005, pp. 3549-3557.
(Continued)

*Primary Examiner* — David A Vanore
(74) *Attorney, Agent, or Firm* — Frommer Lawrence & Haug LLP; Ronald R Santucci (57) ABSTRACT

A control parameter is determined for a system for irradiating a predetermined target volume in a body with a particle beam. The system is constructed to direct the particle beam at a multiplicity of target points in the target volume in succession in order to produce at, each of the target points a predetermined dose distribution in a region around the target point. The control parameter controls the extent of an overlap of the dose distribution of a first target point with the dose distributions of neighboring target points. For determination of the control parameter, there is first determined a movement parameter which quantitatively characterizes the movement of the body at the first target point. The control parameter is determined in dependence on the movement parameter.

24 Claims, 6 Drawing Sheets

U.S. PATENT DOCUMENTS

| | | | |
|---|---|---|---|
| 5,528,651 A * | 6/1996 | Leksell et al. ............... 378/65 |
| 5,969,367 A | 10/1999 | Hiramoto et al. |
| 6,148,272 A | 11/2000 | Bergstrom et al. |
| 6,661,870 B2 | 12/2003 | Kapatoes et al. |
| 6,710,362 B2 * | 3/2004 | Kraft et al. ............... 250/492.3 |
| 6,891,177 B1 * | 5/2005 | Kraft et al. ............... 250/505.1 |
| 7,102,144 B2 | 9/2006 | Matsuda et al. |
| 7,268,358 B2 * | 9/2007 | Ma et al. ............... 250/492.3 |
| 7,792,249 B2 * | 9/2010 | Gertner et al. ............... 378/65 |
| 7,796,731 B2 * | 9/2010 | Nord et al. ............... 378/65 |
| 7,818,045 B2 * | 10/2010 | Rietzel ............... 600/425 |
| 7,906,770 B2 * | 3/2011 | Otto ............... 250/492.3 |
| 7,953,205 B2 * | 5/2011 | Balakin ............... 378/69 |
| 8,045,679 B2 * | 10/2011 | Balakin ............... 378/65 |
| 8,129,699 B2 * | 3/2012 | Balakin ............... 250/492.3 |
| 8,178,859 B2 * | 5/2012 | Balakin ............... 250/492.3 |
| 2005/0167616 A1 | 8/2005 | Yanagisawa et al. |
| 2006/0259282 A1 | 11/2006 | Failla et al. |
| 2007/0034812 A1 | 2/2007 | Ma et al. |
| 2007/0114473 A1 * | 5/2007 | Matsuda et al. ............... 250/505.1 |
| 2007/0228305 A1 * | 10/2007 | Keppel et al. ............... 250/505.1 |
| 2008/0226030 A1 * | 9/2008 | Otto ............... 378/65 |
| 2008/0267349 A1 * | 10/2008 | Rietzel ............... 378/44 |
| 2008/0298550 A1 * | 12/2008 | Otto ............... 378/65 |
| 2009/0095921 A1 | 4/2009 | Bert et al. |
| 2009/0114847 A1 * | 5/2009 | Grozinger et al. ............... 250/492.1 |
| 2009/0161827 A1 * | 6/2009 | Gertner et al. ............... 378/65 |
| 2010/0074408 A1 * | 3/2010 | Bert et al. ............... 378/65 |
| 2010/0301235 A1 * | 12/2010 | Bert et al. ............... 250/492.3 |
| 2010/0322491 A1 * | 12/2010 | Long ............... 382/128 |
| 2010/0327188 A1 * | 12/2010 | Bert et al. ............... 250/492.3 |
| 2012/0008745 A1 * | 1/2012 | Stahl ............... 378/65 |

FOREIGN PATENT DOCUMENTS

| | | |
|---|---|---|
| EP | 1 378 265 A | 1/2004 |
| JP | 2006-087649 A | 4/2006 |
| WO | WO-2007/079854 A | 7/2007 |

OTHER PUBLICATIONS

Kang, Yixiu PHD et al.: "4D Proton Treatment Planning Strategy for Mobile Lung Tumors", *Int. J Radiation Oncology Biol Phys.*, vol. 67, No. 3, 2007, pp. 906-914.

Rietzel, Eike PHD et al.: "Four-Dimensional Image-Based Treatment Planning: Target Volume Segmentation and Dose Calculation in the Presence of Respiratory Motion", *Int. J. Radiation Oncology Biol Phys.*, vol. 61, No. 5, 2005, pp. 1535-1550.

Bert, Christoph: "Bestrahlungsplanung fur bewegte Zielvolumina in der Tumortherapie mit gescanntem Kohlenstoffstrahl", Feb. 3, 2006, dissertation presented in Darmstadt (in German).

Bert, C. et al.: "4D treatment planning for scanned ion beam.", *Radiation Oncology*, Jul. 3, 2007, 2:24. English translation of abstract.

Bert, Christoph: "Bestrahlungsplanung fur bewegte Zielvolumina in der Tumortherapie mit gescanntem Kohlenstoffstrahl", English abstract only, retrieved from Internet http://elib.tu-darmstadt.de/diss.000648, 2006.

International Search Report for PCT/EP2009/001058 from European Patent Office dated Apr. 15, 2009.

* cited by examiner

DETERMINATION OF CONTROL PARAMETERS FOR IRRADIATION OF A MOVING TARGET VOLUME IN A BODY

This application is a 371 of PCT/EP2008/001279 filed on Feb. 19, 2008, published on Oct. 2, 2008 under publication number WO 2008/116535 A which claims priority benefits from German Patent Application Number 10 2007 014 715.7 filed Mar. 23, 2007 and German Patent Application Number 10 2008 008 358.5 filed Feb. 8, 2008, the disclosures of both are incorporated herein by reference.

The present invention relates to a method and apparatus for determination of control parameters of a particle therapy system for irradiation of an at least in some instances moving predetermined target volume in a raster scanning method or in a spot scanning method or in a continuous scanning method or in some other scanning method.

Tumour therapy using particle beams, especially protons, a particles and carbon nuclei, is increasing in importance. In that context, the raster scanning method has a number of advantages over other methods. In this method, a three-dimensional raster is placed over the tumour volume. The particle beam is deflected by deflecting magnets in two directions perpendicular to one another (the x and the y directions). By actively varying the particle energy, the position of the Bragg peak, in which the largest portion of the dose is deposited, is set at differing depths (z direction) in the body.

A number of organs that are of relevance in tumour therapy are located in the vicinity of the lungs and are therefore also caused to move with the movements of the patient's breathing. Control of the particle beam is carried out with reference to a co-ordinate system that does not move with respect to the particle therapy system. Movements of tissue, or of a body, to be irradiated, relative to that co-ordinate system, necessarily have the consequence that there is a disparity between the dose distribution produced in the body and the therapeutically desired dose distribution. These disparities can have an adverse effect on the success of therapy.

The problem of the present invention is to reduce disparities between the dose distribution actually produced in the body and the therapeutically necessary distribution.

The problem is solved by a method according to claim 1 and by an apparatus according to claim 12.

Preferred developments of the present invention are defined in the dependent claims.

The present invention is based on the idea of varying the size of the beam focus, or the lateral dimension of the beam, in the target volume in dependence on the extent of the movement of the body or sub-regions of the body. In particular, the diameter of the particle beam is varied in dependence on the amplitude and/or speed of the movement of the body or sub-regions of the body. In the process, besides taking into account movements or time dependences of the target volume, movements or time dependences of regions lying in front of the target volume in the beam direction are also taken into account.

A region, of the body to be irradiated, that is not moving or that is moving only insubstantially is irradiated using a small beam focus, for example using the minimum beam focus that is possible. A moving region is irradiated using an enlarged focus or a widened beam having an enlarged diameter or broader beam profile. A monotonic relationship between the extent of the movement and the diameter of the beam is advantageous. The described widening of the beam focus is, above all, advantageous in the case of movement of the body in a direction perpendicular to the beam.

The present invention is furthermore based on the idea of widening the Bragg peak of the particle beam in dependence on the extent of a movement of a body in order, alternatively or additionally, also in the case of a movement of the body parallel to the beam direction (z direction), to reduce the effect thereof on the dose distribution produced. Those regions of the body to be irradiated that do not move—or that move only insubstantially—in the z direction are irradiated using a sharply defined particle energy and a correspondingly sharp Bragg peak. Those regions that do move in the z direction are irradiated with particles whose energy distribution has an increased width and whose Bragg peak is likewise correspondingly widened. Here too, a monotonic relationship between the extent of the movement and the widths of the lack of energy sharpness and of the Bragg peak is advantageous.

It is possible either for the size of the beam focus or the beam diameter and/or the width of the Bragg peak to be set for the target volume as a whole at values that are dependent on the extent of the movement or motion but dependent on the location or, alternatively, for the beam diameter and the width of the Bragg peak to be varied within the target volume and to take location-dependent values. In the latter case, regions that move only slightly within the target volume are irradiated using a smaller beam diameter and/or a narrower Bragg peak than regions that move more.

The extent of the movement or motion of a region of a body can be ascertained in the run-up to irradiation planning, for example by means of time-resolved tomographic methods (for example, time-resolved computed tomography—4DCT—or time-resolved nuclear spin tomography). Alternatively, it is possible to use a multiplicity of tomographic images that have not been obtained at short time intervals but that do provide statistical information relating to movements in the target volume. Alternatively or additionally, the movement in the target volume is determined by suitable sensors. For that purpose, for example, the breathing movements of the thorax are determined by a sensor.

When the movement of the body in the target volume is determined during the irradiation, the above-described movement-dependent adjustment of the beam focus and/or of the Bragg peak can be combined with a gating. In that case, the irradiation is carried out exclusively when the body to be irradiated is in a defined movement state or in a predetermined interval of movement states.

The invention will be explained in greater detail hereinbelow by way of example with reference to the accompanying Figures, in which.

Figure 1:
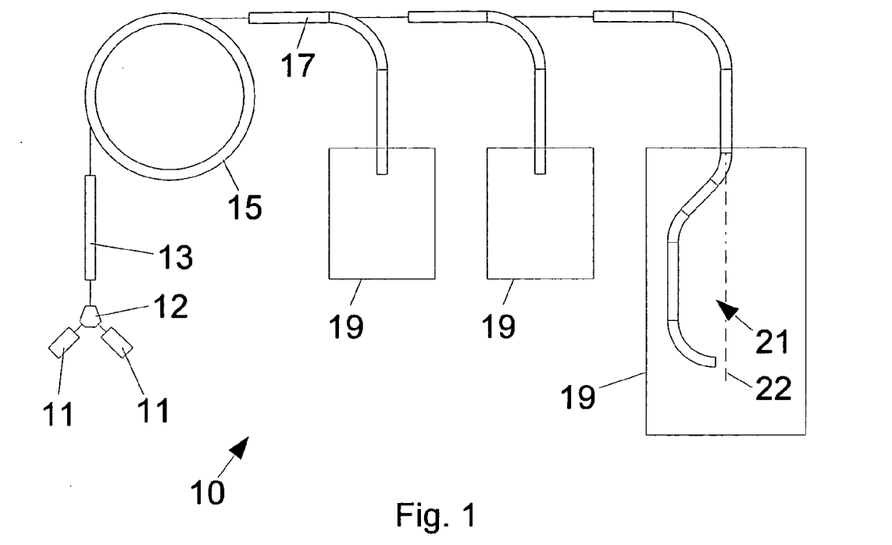
FIG. 1 shows, in diagrammatic form, a particle therapy system.

FIG. 1 shows, in diagrammatic form, an overview of the structure of particle therapy system 10. In a particle therapy system 10, a body, especially tissue with tumour disease, is irradiated with a particle beam. The particles used are, in the main, ions such as, for example, protons, pions, helium ions, carbon ions or other ion types.

Usually, such particles are produced in a particle source 11. If, as shown in FIG. 1, there are provided two particle sources 11, which produce two different ion types, it is possible to switch over between those two ion types within a short time interval. For this purpose there is used, for example, a switching magnet 12 arranged between, on the one hand, the ion sources 11 and, on the other hand, a pre-accelerator 13.

Examples that may be mentioned of two different ion types which can be alternatively used in a particle therapy system are helium ions ($^3$He or $^4$He) and carbon ions. These differ in the biological effect of their beams and are suitable for different types of tumours. $^4$He and $^{12}$C both have, in the fully ionised state, the same A/Q ratio between the mass number A and charge Q. They can therefore be accelerated in the same acceleration system without major adaptation.

The ions produced by the or by one of the ion source(s) 11 and, where applicable, selected using the switching magnet 12 are accelerated to a first energy level in the pre-accelerator 13. The pre-accelerator 13 is, for example a linear accelerator (LINAC for: "LINear ACcelerator"). The particles are then fed into an accelerator 15, for example a synchrotron or cyclotron. In the accelerator 15 they are accelerated to high energies as are required for the purpose of irradiation. After the particles leave the accelerator 15, a high-energy beam transport system 17 guides the particle beam to one or more irradiation rooms 19. In an irradiation room 19, the accelerated particles are directed at a body to be irradiated. Depending on the particular arrangement, this is carried out from a fixed direction (in so-called "fixed beam" rooms") or, however, by means of a rotatable gantry 21 which can be moved about an axis 22, from different directions.

The basic structure, shown by FIG. 1, of a particle therapy system 10 is typical of many particle therapy systems but can also differ therefrom. The exemplary embodiments described hereinbelow can be used both in conjunction with the particle therapy system shown by FIG. 1 and also with other particle therapy systems.

Figure 2:
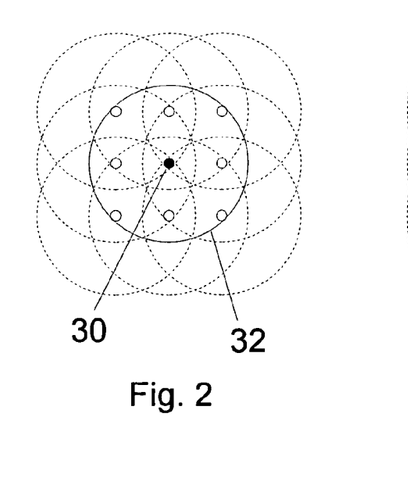
FIG. 2 shows, in diagrammatic form, a dose distribution in an isoenergy layer.
Figure 3:
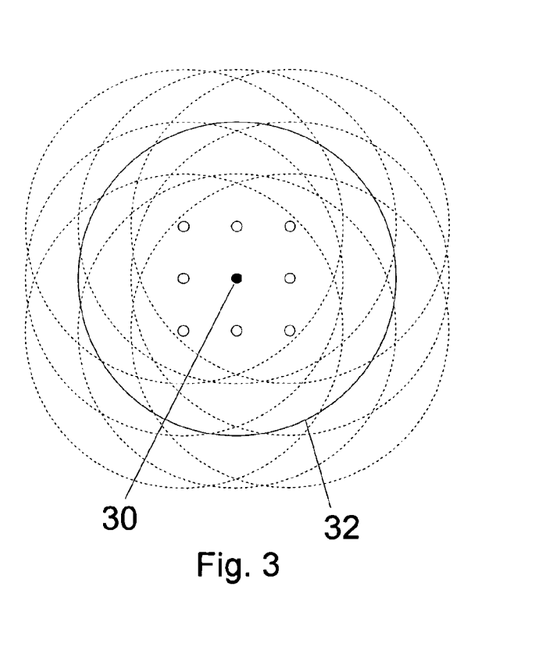
FIG. 3 shows, in diagrammatic form, a dose distribution in an isoenergy layer.

FIGS. 2 and 3 show, in diagrammatic form, the dose distribution in an isoenergy layer. An isoenergy layer is a layer in which the Bragg peaks of particle beams of a particular energy are located. When the body is homogeneous, especially having a homogeneous density and a homogeneous isotope composition, in the beam direction in front of the isoenergy layer under consideration, the isoenergy layer is planar. When the density or the composition of the body varies spatially in the beam direction in front of the isoenergy layer under consideration, the isoenergy layer usually departs from the planar form.

A three-dimensional raster is laid over the body to be irradiated. In an isoenergy layer there is located, for example, a square grid of pixels or target points 30, nine of which are shown by way of example in FIG. 2. In the isoenergy layer the particle beam is directed at each target point for a predetermined period of time and/or using a predetermined intensity or predetermined particle flow output in order to produce a predetermined dose in the immediate vicinity of the target point. The dose distribution within the isoenergy layer resulting from the irradiation of an individual target point corresponds approximately to the particle flow distribution or lateral profile of the particle beam. As a good approximation, the beam profile can often be approximated by a Gauss function or bell.

The dose distributions due to the irradiation of the individual target points are indicated in FIG. 2 by lines 32. These lines represent locations of identical dose, for example locations where the dose is 50% of the maximum dose. These locations are, in the ideal case, located on a circle. The spatial distribution of the dose resulting from the irradiation of the middle pixel (which pixel is shown as a filled-in circle) is in each case shown by a solid line; the dose distributions resulting from the irradiation of the other pixels (which are shown as small empty circles) are shown by broken lines.

FIG. 2 shows the dose distributions for a particle beam having a small focus or small beam diameter. The dose distributions due to the individual target points overlap to a relatively small extent. The dose produced at each point in the isoenergy layer substantially results from just a few target points 30. The small focus or beam diameter has the consequence that the dose drops off relatively steeply at the edge of the target volume and is, however, unsuitable for regions of the body that are moving.

FIG. 3 shows the dose distributions for a particle beam having a large focus or large beam diameter. The dose distributions due to the individual target points overlap to a relatively great extent. The dose produced at each point in the isoenergy layer results in each case from the irradiation of many target points 30. The large focus or beam diameter is, as shown hereinbelow with reference to FIGS. 4 to 7, suitable for a moving body or a moving region of a body.

FIGS. 4 to 7 show, in diagrammatic form, dose distributions along a line in an isoenergy layer. The Figures in each case show a diagram wherein the abscissa is associated with a co-ordinate x along the line in the isoenergy layer and the ordinate with the dose D, said line being so located in the isoenergy layer that a number of target points of the particle beam are located on the line.

In all the examples shown in FIGS. 4 to 7, the target points are arranged in a uniform raster in a co-ordinate system that does not move with respect to the irradiation system. In the non-moving co-ordinate system, therefore, all pairs of closest neighbouring target points have the same spacing from one another. The line and the co-ordinate x do not move relative to the body to be irradiated. When the body or regions of the body move(s) relative to the co-ordinate system of the irradiation system in a direction parallel to the line, the co-ordinates x of the target points change.

In each case, FIGS. 4 to 7 show the dose distributions 42 resulting from irradiations of the individual target points and the dose distribution 50 resulting from the irradiation as a whole (total dose). The dose distribution 50 is therefore in each case the sum of the dose distributions 42.

Figure 4:
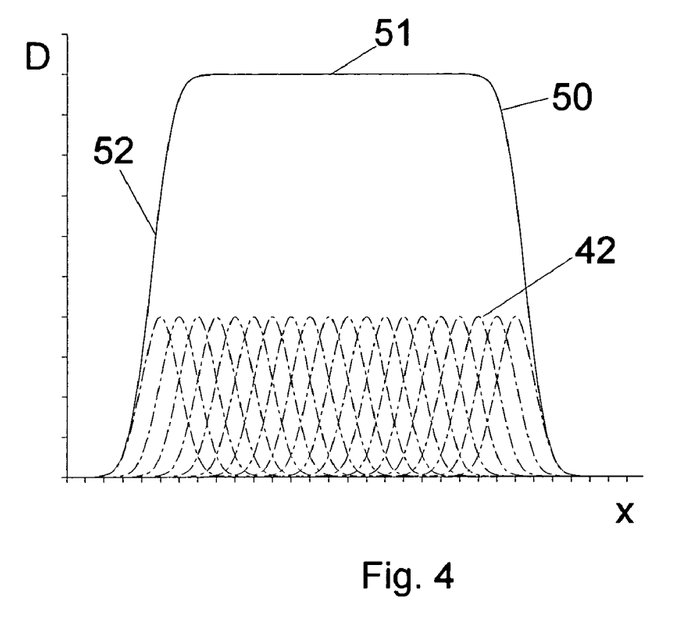
FIG. 4 shows, in diagrammatic form, a dose distribution along a line in an isoenergy layer.

FIG. 4 shows the dose distributions 42, 50 in the case of a body which does not move relative to the irradiation system. The dose distributions 42 resulting from irradiations of the individual target points are, because the body is not moving, arranged just as uniformly as the target points in the co-ordinate system of the irradiation system. The dose distribution 50 resulting from the irradiation of all the target points therefore has a flat plateau region 51 having a dose D substantially independent of the co-ordinate x. Relatively steep flanks 52 at the edge of the flat plateau region 51 are located at the edges of the target volume in the body.

Figure 5:
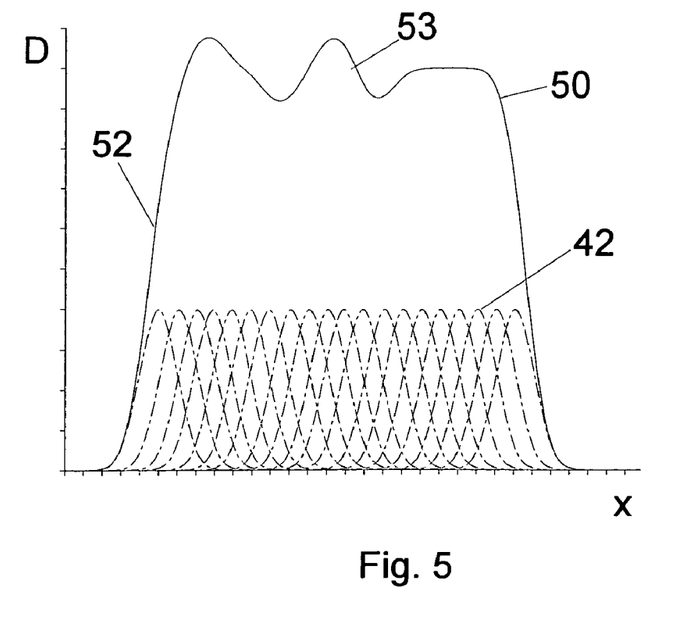
FIG. 5 shows, in diagrammatic form, a dose distribution along a line in an isoenergy layer.

FIG. 5 shows the dose distributions 42, 50 in the case of a body that does move. Movements of the body in the direction parallel to the line during the sequential irradiation of the individual target points have the consequence that the resulting dose distributions 42 are no longer uniformly distributed in the body with respect to the co-ordinate x. Even the small non-uniformities which can be seen in FIG. 5 only on close inspection have the consequence that the dose distribution 50 resulting from the irradiation as a whole no longer has a flat plateau region 51. In its stead, pronounced spatial variations 53 in the dose D can be seen. These spatial variations 53 in the dose D represent disparities with respect to the therapeutically optimum dose within the target volume and jeopardise the success of therapy.

Figure 6:
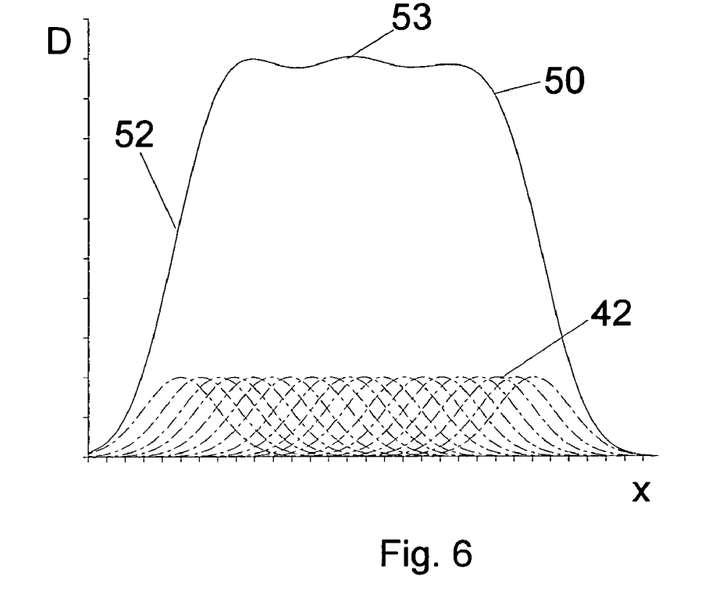
FIG. 6 shows, in diagrammatic form, a dose distribution along a line in an isoenergy layer.

FIG. 6 shows the dose distributions 42, 50 for the same situation as that also shown in FIG. 5, especially the same movements of the body. In contrast to FIG. 5, however, a larger beam diameter or beam focus was selected. The dose distributions 42 resulting from the irradiations of the individual target points or from directing the particle beam at the individual target points are therefore flatter and wider. The dose distribution 50 resulting from the radiation as a whole has spatial variations 53 which are substantially lower than in the case of the smaller beam diameter shown hereinbefore with reference to FIG. 5.

Figure 7:
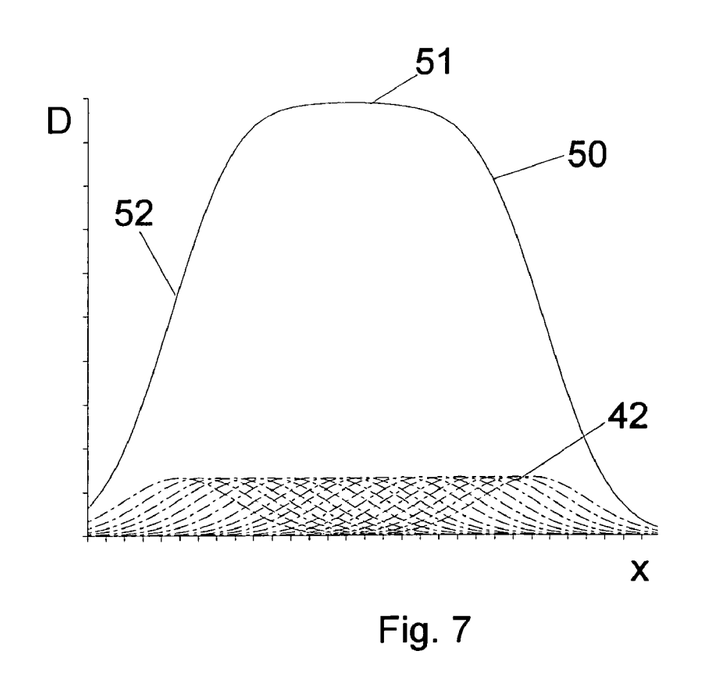
FIG. 7 shows, in diagrammatic form, a dose distribution along a line in an isoenergy layer.

FIG. 7 shows the dose distributions 42, 50 for the same situation, especially for the same movements of the body during irradiation as form the basis for the illustrations of FIGS. 5 and 6. The beam diameter or beam focus is, however, enlarged even further compared to the illustration in FIG. 6. The dose distributions 42 resulting from the individual irradiations of the target points are correspondingly even flatter and wider. Despite the movement of the body during the sequential irradiation of the target points, the dose distribution 50 resulting from the irradiation as a whole has a substantially flat plateau region 51.

Consequently, as a result of the enlargement of the diameter of the particle beam, the influence that movements of the body during the sequential irradiation have on the dose distribution 50 resulting from the irradiation as a whole can be suppressed entirely or at least to a level that is acceptable.

A comparison of FIGS. 5, 6 and 7 shows that an increasing particle beam diameter has the consequence of a decreasing steepness of the flanks 52 of the dose distribution 50 resulting from the irradiation as a whole. Using an optimised relationship between the extent of the movement of the body and the beam diameter to be set it is possible to obtain sufficient homogeneity of the dose D with acceptable spatial variations within the target volume and, at the same time, flanks of the dose D at the edge of the target volume that are as steep as possible. For the purpose, there is selected, for example, a monotonic, especially strictly monotonic, relationship between the movement of the body in the region of a target point and the beam diameter to be selected when directing the particle beam at the target point.

Figure 8:
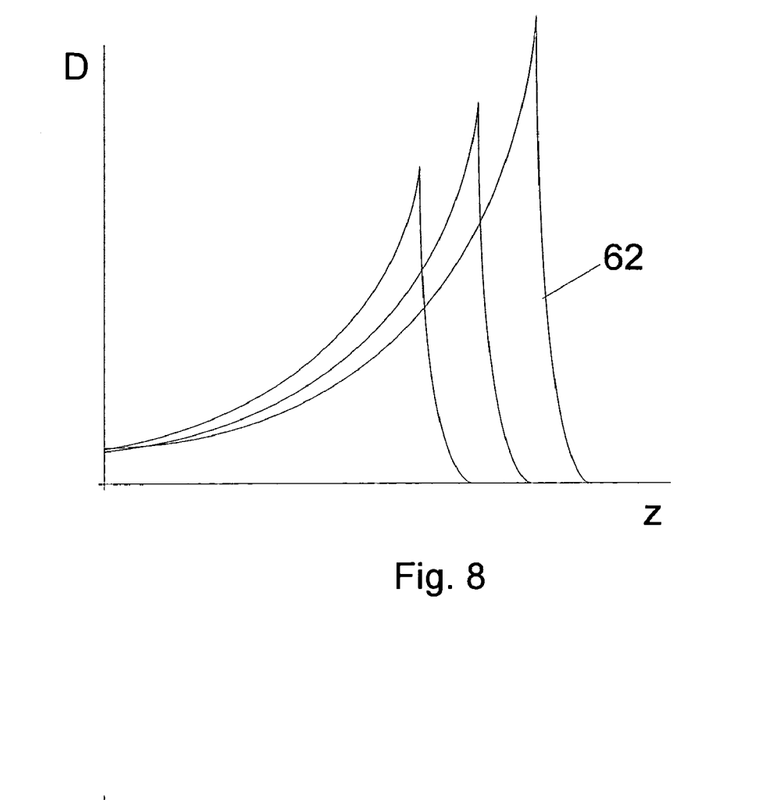
FIG. 8 shows, in diagrammatic form, a dose distribution along a line parallel to the particle beam.
Figure 9:
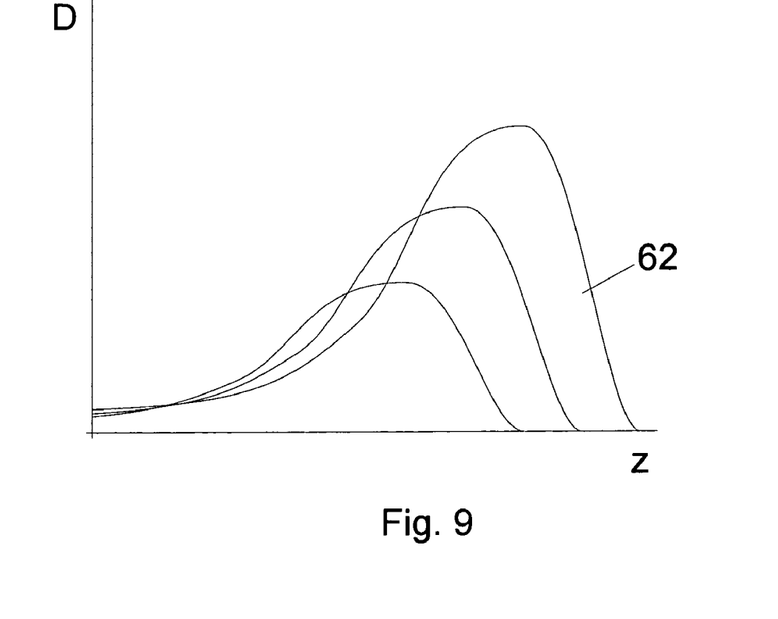
FIG. 9 shows, in diagrammatic form, a dose distribution along a line parallel to the particle beam.

FIGS. 8 and 9 show, in diagrammatic form, dose distributions along a line parallel to the particle beam. In each case, the abscissa is associated with a co-ordinate z along that line; in each case, the ordinate is associated with the dose D. In each case, the dose distributions 62 resulting from the irradiation of three isoenergy planes, that is to say using three nominal particle energies, are shown.

FIG. 8 shows the dose distributions 62 for three sharply defined particle energies, resulting in the more or less pronounced (depending on the particle mass) Bragg peaks known for monoenergetic particle beams. In a manner similar to that shown above with reference to FIG. 5 for a movement of the body along an isoenergy layer, movements of the body in a direction parallel to the particle beam result in non-homogeneity of the dose distribution resulting from the irradiation of all the isoenergy planes. Changes in density due to movement in any direction can also result in changes when they are located in the entry channel of the beam, that is to say in regions lying in front of the target volume in the beam direction.

FIG. 9 shows dose distributions 62 as are produced by particle beams having wider energy distributions. The Bragg peaks are less pronounced; the dose distributions 62 are wider and flatter. In a manner similar to that shown above with reference to FIGS. 6 and 7 for an enlargement of the beam diameters, the dose distributions shown in FIG. 9, which are wider in the beam direction, result in a suppression of the influence that movements of the body or of parts of the body in the direction of the particle beam during the sequential irradiation of the isoenergy layers have on the dose distribution resulting from the irradiation as a whole. Furthermore, because of the wider Bragg peaks, movements or changes in density in the entry channel or in regions which are located in front of the target volume in the beam direction also have less influence on the desired dose distribution.

Widening the energy distribution of a particle beam originally produced by a particle accelerator in substantially monoenergetic form is possible, for example, using a ripple filter.

When a movement of a body to be irradiated has, in the target volume, components that are parallel to the isoenergy planes as well as parallel to the particle beam or when, for example, in addition to a movement of the target volume or within the target volume in a direction perpendicular to the beam, there is also a time-dependent density in the entry channel, the widening of the particle beam shown above with reference to FIGS. 6 and 7 can be combined with the broadening of the energy distributions of the particle beam shown above with reference to FIG. 9.

An enlargement of the overlap of the dose distributions resulting from the irradiations of the individual target points can be obtained not only by widening the particle beam or the energy distribution of the particle beam. Alternatively or additionally, within each isoenergy layer there is selected a tighter raster of target points and/or a tighter sequence of isoenergy layers.

The variation, shown above with reference to FIGS. 2, 3, 8 and 9, in the overlap of the dose distributions in a direction perpendicular to the particle beam (FIGS. 2 and 3) and in a direction parallel to the particle beam (FIGS. 8 and 9) and also the mentioned variation in the spacing of the isoenergy layers can also be carried out systematically as a function of the particle energy or of an isoenergy layer number. As a result it is possible to modify the irradiation flexibly and also, under certain circumstances, to speed it up.

The further proximal that a target point is arranged, or the lower the particle energy that is associated with a target point, the greater is the dose which is produced at that target point by the irradiation of target points using higher particle energy. This dose component resulting from the irradiation of more deeply located target points has a relatively low degree of location dependency. The greater that dose component, the less is the influence that the location dependency of the dose produced by the irradiation of the target point under consideration has on the accuracy with which the actually deposited dose corresponds to the prescribed dose.

Therefore, when irradiating a proximal, or less deeply located, layer (for example, shown in FIGS. 8 and 9 by the Bragg peak arranged in each case on the left), the extent of the overlap of the individual dose distributions can be smaller than when irradiating a distal, or more deeply located, layer (for example, shown in FIGS. 8 and 9 by the Bragg peak arranged in each case on the right). As a result of an isoenergy layer spacing that is larger in the case of proximal isoenergy layers, the number of isoenergy layers and also, as a result, the number of target points as a whole can be reduced. A reduction in the number of isoenergy layers or in the number of target points results in speeding-up of the irradiation procedure as a whole, which is beneficial to the patient and to the economic viability of operation of the particle therapy system.

In the above description, the stated objective has primarily been to produce a homogeneous dose distribution or a dose that is independent of location within the target volume. The measures described above with reference to FIGS. 2 to 9 are, however, equally suitable for obtaining a prespecified non-homogeneous dose distribution in spite of movement, or time-dependent non-homogeneity, of the target volume or of regions located in front thereof in the beam direction.

Figure 10:
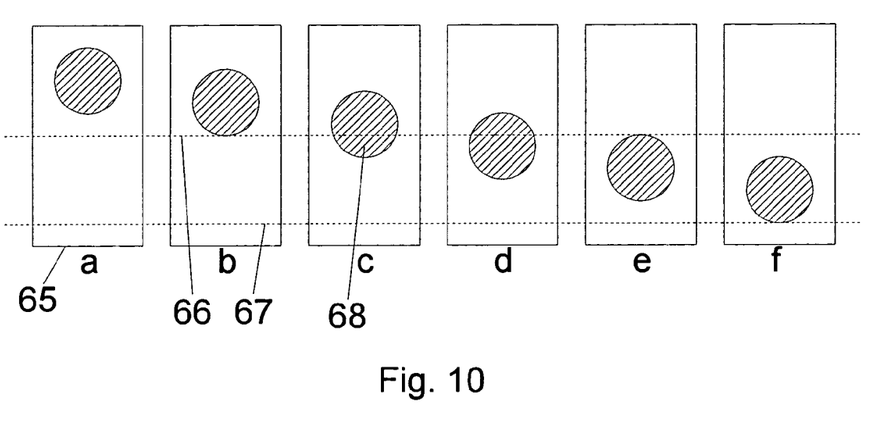
FIG. 10 shows, in diagrammatic form, a movement of a region of a body to be irradiated.

FIG. 10 shows, in diagrammatic form, a combination of the measures described above by means of FIGS. 3, 6, 7 and 9 with a gating. FIG. 10 shows different movement states of a body, which are identified by the letters a to f. As a reference in each case there is depicted an observation window 65, which is stationary in the co-ordinate system of the irradiation system. Furthermore, there are shown a first edge 66 and a second edge 67 of a gating window. In the sequence of movement states a to f, an observed region 68, for example a tumour or some other clinical target volume, moves into the gating window from above. The observed region 68 is located completely outside the gating window in the movement states a and b and partially outside the gating window in the movement states c and d. In the movement states e and f, the observed region is located completely inside the gating window. An irradiation occurs only in the movement states e to f, in which states the observed region 68 is located completely inside the gating window. This ensures that regions of the body within the target volume are displaced with respect to a desired location at the moment of irradiation only to an extent defined by the gating window or by the difference between the dimensions of the gating window and the observed region 68. In order to suppress the influence that the remaining movement of the body during the irradiation has on the dose distribution resulting from the irradiation as a whole, the extent of the overlap between the dose distributions of the individual target points is increased, as described above.

The above illustrations by means of FIGS. 2 to 10 relate to a three-dimensional raster or two-dimensional section thereof. This raster can, in contrast to the illustration in FIGS. 2 to 9, have periods that are different in the three spatial directions, that is to say can be non-cubic, and/or have different numbers of grid points in different spatial directions or as a whole and/or have different numbers of raster points in parallel planes. Furthermore, a hexagonal or also any other desired raster is possible.

The above-described measures can be used for any irradiation wherein a particle beam is directed at a multiplicity of target points in succession in a continuous or non-continuous process. For example, the described measures can be used for a spot scanning method, wherein the particle beam remains at each target point for a predetermined time and/or deposits a predetermined number of particles and is switched off while deflecting magnets are set for the next target point. The method can furthermore be used for a raster scanning method, wherein the particle beam remains at each target point for a predetermined period of time and/or deposits a predetermined number of particles but is not, or not always, switched off between the target points.

The above-described measures are furthermore suitable for a continuous scanning method. In a continuous scanning method, the target points form continuous lines, that is to say they form continuous (or quasi-continuous) sets, the number of which is countably infinite. In a continuous scanning method, the particle beam is continuously deflected at least within a line or row within an isoenergy layer and passes over the target points without remaining for a time at individual locations.

Instead of a beam diameter that is dependent on the extent of the movements of the body to be irradiated, a reduction in the scanning speed is also possible in the case of a continuous scanning method. At the same time, in this case, the particle rate, or the number of particles in the particle beam per unit time, is reduced in order that the dose obtained at each location is the same.

Figure 11:
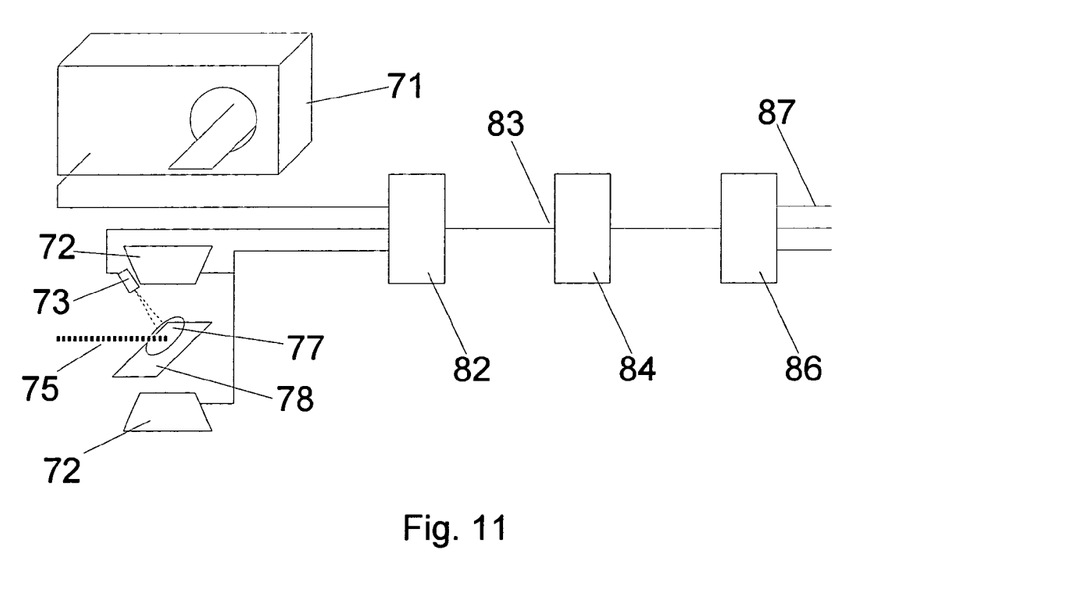
FIG. 11 shows, in diagrammatic form, an apparatus for the determination of a control parameter of a particle therapy system.

FIG. 11 shows, in diagrammatic form, an apparatus for determination of a control parameter of a system for irradiating a predetermined target volume in a body with a particle beam. The apparatus comprises a device 82 for determination of a movement parameter and a device 84 for determination of a control parameter. The device 84 receives the movement parameter from the device 82 and, in dependence thereon, determines the control parameter. The device 82 for determination of a movement parameter is connected to, for example, a computed tomography device 71 or a nuclear spin tomography device for producing time-resolved tomographic images or an X-ray device for (two-dimensional) fluoroscopy of the body to be irradiated.

Alternatively or additionally, the device 82 is connected to a PET camera (PET=Positron Emission Tomography), which is provided at the body irradiation site or in another room in order to detect during irradiation, or immediately after irradiation, photon pairs which are released when positrons are annihilated. The PET camera 72 supplies the device 82 with an image of the dose distribution produced in the irradiated body 77.

Alternatively or additionally, the device 82 is connected to an ultrasonic sensor 73 or some other sensor for detection of the movement, during the irradiation, of the body 77 being irradiated.

The device 82 receives from the tomography device 71 a plurality of time-resolved images of the body to be irradiated. Alternatively or additionally, during irradiation of the body 77 resting on a support surface 78 with a particle beam 75, the device 82 receives a measurement signal from the sensor 73. This measurement signal indicates the momentary movement state of the body 77. Alternatively or additionally, the device 82 receives from the PET camera 72 an image of the dose distribution produced by the particle beam 75 in the body 77. The device 82 determines, from those input data items, one or more movement parameters which quantitatively characterise the movement of the body at least at a first target point. If the input data items are sufficiently comprehensive and accurate, a movement parameter can be determined for each target point within the target volume or for each of a plurality of groups of target points.

The movement parameter(s) determined by the device 82 is/are transferred to an input 83 of the device 84 for determination of the control parameter. The device 84 determines one or more control parameters in dependence on the movement parameter or movement parameters. These control parameters are transferred to a control device 86. The control device 86 controls a system of a kind shown, for example, hereinbefore by FIG. 1. Under the control of the control device, the system directs the particle beam 75 at a multiplicity of target points in a target volume in the body 77 in succession in order to produce at each of the target points a predetermined dose distribution in a region around the target point. The control parameter(s) transferred by the device 84 to the control device 86 control(s) the extent of an overlap of the dose distributions of each of the target points with the dose distributions of the respectively neighbouring target points. The extent of the overlap is, as described, for example, hereinbefore with reference to FIGS. 3, 6, 7 and 9, varied for the target volume as a whole in location-independent or location-dependent manner.

In contrast to the above illustration by means of FIG. 11, the devices 82 and 84 or also the devices 82, 84 and 86 can furthermore be integrated in a single device or in a single system, for example in an irradiation planning system.

The device 84 can be constructed to control or to carry out a method as shown hereinbelow with reference to FIG. 12.

Figure 12:
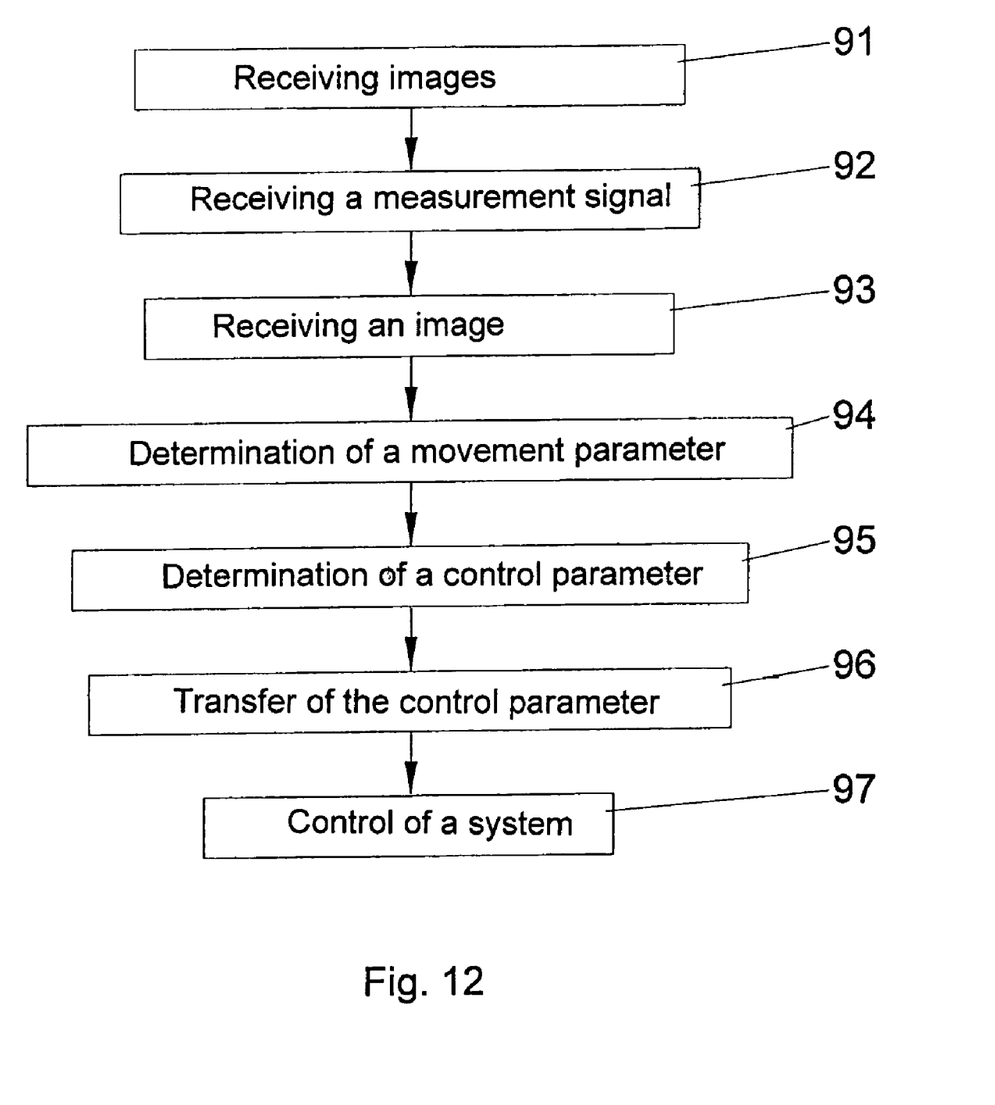
FIG. 12 shows, in diagrammatic form, a flow diagram of a method for determination of control parameters of a particle therapy system.

FIG. 12 shows, in diagrammatic form, a flow diagram of a method for determination of a control parameter for a system for irradiating a predetermined target volume in a body with a particle beam. The method is arranged for a system which directs the particle beam at a multiplicity of target points in the target volume in succession in order to produce at each of the target points a predetermined dose distribution in a region around the target point. The control parameter therein controls the extent of an overlap of the dose distribution of a first target point with the dose distribution of neighbouring target points.

In a first step 91, a plurality of time-resolved images, especially tomograms, of the body to be irradiated are received. These images can have been formed immediately before irradiation or before the start of an irradiation programme comprising a plurality of irradiations or also a period of several days or weeks beforehand. Alternatively or additionally, a measurement signal of a sensor which detects a movement of the body during the irradiation is received in a second step 92. This sensor can be, for example, the ultrasonic sensor 78 shown hereinbefore by FIG. 10. Alternatively or additionally, an image, during irradiation, of the body being irradiated is received in a third step 93. For example, this image is a tomogram produced using the PET camera described hereinbefore with reference to FIG. 10. Alternatively, fluoroscopy, or continuous two-dimensional projection X-raying, can be used.

In a fourth step 94, one or more movement parameter(s) is/are determined from one or more of the input data item(s) received in the first step 91, the second step 92 and the third step 93. This is performed, for example, in the device 82 shown hereinbefore by FIG. 10.

In a fifth step 95, one or more control parameter(s) is/are determined in dependence on the movement parameter(s). This is performed, for example, in the device 84 shown hereinbefore by FIG. 10. The control parameter(s) determined is/are provided for controlling, in the irradiation system, the extensions of the dose distributions at, in each case, at least one target point and/or spacings between neighbouring target points. The control parameter(s) is/are especially provided, for example, for controlling the lateral profile or the width of the Bragg peak of the particle beam at, in each case, at least one of the target points.

When the movement parameter(s) is/are obtained from input data items obtained during irradiation of the body, the control parameters can be provided in order to control an irradiation of the body exclusively in movement states from a predetermined set of movement states. For example, the predetermined set of movement states is so selected that in those movement states a disparity in the local total dose with respect to a desired value, which disparity results from the movement of the body, can be adequately suppressed by means of an overlap of the dose distributions at the target points. In that case, the movement parameter(s) also characterise(s) the movement of the body, for example, only in the movement states from the predetermined set of movement states.

In a sixth step 96, the control parameter(s) is/are transferred to the irradiation system. This is accomplished, for example, in the exemplary embodiment shown hereinbefore by FIG. 10, between the device 84 for determination of a control parameter and the control device 86. In a seventh step 97, a system for irradiation of the planning target volume, of a kind shown, for example, hereinbefore by FIG. 1, is controlled using the control parameter(s).

The above-described steps can be carried out in a plurality of separate methods and at different points in time. For example, the first step 91, the fourth step 94 and the fifth step 95 are carried out immediately before the irradiation or also even some days or weeks beforehand in a separate method. Alternatively or additionally, for example, the second step 92 and/or the third step 93 and also the fourth step 94 and the fifth step 95 are carried out immediately before or during the irradiation in a separate method. In both examples, the sixth step 96 and the seventh step 97 can be in the form of one or two separate methods which are carried out immediately after the other steps or spaced apart therefrom in time.

The exemplary embodiments described are suitable not only for use in the context of particle therapy. In addition, they can be used generally in systems for the irradiation of material, especially when the applied beam dose should vary spatially or be restricted to a target volume, and especially when the material moves relative to the reference system of the system or is moved relative to the reference system of the system.

List of Reference Numerals
10 particle therapy system
11 particle source
12 switching magnet
13 pre-accelerator
15 accelerator
17 high-energy beam transport system
19 irradiation room
21 gantry
22 axis of gantry 21
30 target point
32 actual extension of the beam at target point 30
42 dose distribution resulting from beam at one target point
50 dose distribution resulting from irradiation as a whole
51 flat plateau region
52 flank
53 spatial variation of the dose
62 dose distribution from an isoenergy plane
65 observation window
66 first edge of a gating window
67 second edge of the gating window
68 observed region
71 tomography device
72 PET camera
73 ultrasonic sensor
75 particle beam
77 body
78 support surface
82 device for determination of a movement parameter
83 input of device 84
84 device for determination of a control parameter
86 control device for irradiation system
87 control line
91 first step
92 second step 93 third step
94 fourth step
95 fifth step
96 sixth step
97 seventh step

The invention claimed is:

1. Method of determining a control parameter of a system for irradiating a predetermined target volume in a body with a particle beam, the system being constructed to direct the particle beam at a multiplicity of target points in the target volume in succession in order to produce at each of the target points a predetermined dose distribution in a region around the target point, wherein the control parameter controls the extent of an overlap of the dose distribution of a first target point with the dose distributions of neighbouring target points, comprising the following steps:
  determination of a movement parameter which quantitatively characterises the movement of the body at the first target point;
  determination of the control parameter in dependence on the movement parameter.

2. Method according to claim 1, wherein the control parameter is provided for controlling the extension of the dose distribution at the first target point and/or the spacing of the first target point from neighbouring target points.

3. Method according to of claim 1, wherein the control parameter is provided for controlling the lateral profile of the particle beam at the first target point.

4. Method according to claim 1, wherein the control parameter is provided for controlling the width of a Bragg peak of the particle beam at the first target point.

5. Method according to claim 1, wherein a plurality of images of the body which have been determined at different points in time before the irradiation enter into the determination of the movement parameter.

6. Method according to claim 1, wherein an image of the body during the irradiation enters into the determination of the movement parameter.

7. Method according to claim 1, wherein a measurement signal of a sensor which detects the movement of the body enters into the determination of the movement parameter.

8. Method according to claim 1, wherein the movement parameter characterises an amplitude or speed of the movement.

9. Method according to claim 1, wherein the movement parameter characterises the movement of the body only in a time interval in which the body is in a movement state from a predetermined set of movement states.

10. Method according to claim 9, wherein the predetermined set of movement states includes movement states in which disparities in the local total dose with respect to a desired value that result from the movement of the body can be held within a given range by means of a given maximum overlap of the dose distributions at the target points.

11. Method according to claim 9, wherein the control parameters are provided for the control of an irradiation which takes place only in the time interval in which the body is in a movement state from the predetermined set of movement states.

12. Method according to claim 1, wherein the control parameter is additionally varied in dependence on the depth of a target point to be irradiated or on the particle energy.

13. Method according to claim 12, wherein the control parameter is varied so that the extent of the overlap of the dose distributions of neighbouring target points is greater in the case of a more deeply located target point than in the case of a less deeply located target point or is greater in the case of a higher particle energy than in the case of a lower particle energy.

14. Apparatus for determination of a control parameter of a system for irradiating a predetermined target volume in a body with a particle beam, the system being constructed to direct the particle beam at a multiplicity of target points in the target volume in succession in order to produce at each of the target points a predetermined dose distribution in a region around the target point, wherein the control parameter controls the extent of an overlap of the dose distribution of a first target point with the dose distributions of neighbouring target points, having the following features:
  an input for receiving a movement parameter which characterises the movement of the body at the first target point;
  a device for determination of the control parameter in dependence on the movement parameter.

15. Apparatus according to claim 14, wherein the control parameter is provided for controlling the extension of the dose distribution at the first target point and/or the spacing of the first target point from neighbouring target points.

16. Apparatus according to claim 14, wherein the control parameter is provided for controlling the lateral profile of the particle beam at the first target point.

17. Apparatus according to claim 14, wherein the control parameter is provided for controlling the width of a Bragg peak of the particle beam at the first target point.

18. Apparatus according to claim 14, further having:
  a device for receiving a plurality of images of the body which have been determined at different points in time before the irradiation and for determination of the movement parameter in dependence on the image.

19. Apparatus according to claim 14, further having:
  a device for receiving an image of the body during the irradiation and for determination of the movement parameter in dependence on the image.

20. Apparatus according to claim 14, further having:
  a device for receiving a measurement signal of a sensor which detects the movement of the body and for determination of the movement parameter in dependence on the measurement signal.

21. Apparatus according to claim 14, wherein the apparatus is a therapy planning apparatus.

22. Apparatus according to claim 14, wherein the device for determination of the control parameter is constructed to vary the control parameter additionally in dependence on the depth of a target point to be irradiated or on the particle energy.

23. Apparatus according to claim 22, wherein the device for determination of the control parameter is constructed to vary the control parameter so that the extent of the overlap of the dose distributions of neighbouring target points is greater in the case of a more deeply located target point than in the case of a less deeply located target point or is greater in the case of a higher particle energy than in the case of a lower particle energy.

24. System for irradiating a predetermined target volume in a body with a particle beam, the system directing the particle beam at a multiplicity of target points in the target volume in succession in order to produce at each of the target points a predetermined dose distribution in a region around the target point, wherein the control parameter controls the extent of an overlap of the dose distribution of a first target point with the dose distributions of neighbouring target points, and wherein the system comprises an apparatus according to claim 14.

* * * * *